(12) United States Patent
Geyer et al.

(10) Patent No.: US 8,829,429 B2
(45) Date of Patent: Sep. 9, 2014

(54) FUNCTIONAL CHECK AND VARIANCE COMPENSATION IN MASS SPECTROMETRY

(75) Inventors: Roland Geyer, Mattmenstetten/Rossau (DE); Werner Halg, Mannedorf (CH); Michael Vogeser, Munich (DE)

(73) Assignee: Tecan Trading AG, Mannedorf (CH)

( * ) Notice: Subject to any disclaimer, the term of this patent is extended or adjusted under 35 U.S.C. 154(b) by 495 days.

(21) Appl. No.: 13/379,180

(22) PCT Filed: Jun. 18, 2010

(86) PCT No.: PCT/EP2010/058665
§ 371 (c)(1),
(2), (4) Date: Apr. 13, 2012

(87) PCT Pub. No.: WO2010/149595
PCT Pub. Date: Dec. 29, 2010

(65) Prior Publication Data
US 2012/0187284 A1 Jul. 26, 2012

(30) Foreign Application Priority Data
Jun. 25, 2009 (DE) .......... 10 2009 030 395

(51) Int. Cl.
*H01J 49/00* (2006.01)
*G01N 30/02* (2006.01)
(52) U.S. Cl.
CPC ......... *H01J 49/0009* (2013.01); *H01J 49/0036* (2013.01); *G01N 30/02* (2013.01)
USPC ............. 250/288; 250/281; 250/282

(58) Field of Classification Search
CPC ... G01N 30/7233; G01N 30/02; G01N 30/72; G01N 30/8675; G01N 30/8624; G01N 30/8644; G01N 2030/027; H01J 49/0027
USPC .................. 250/281, 282, 286, 288
See application file for complete search history.

(56) References Cited

U.S. PATENT DOCUMENTS

2004/0108452 A1* 6/2004 Graber et al. ............ 250/281
2009/0250607 A1* 10/2009 Staats et al. ............. 250/282

* cited by examiner

*Primary Examiner* — Nicole Ippolito
*Assistant Examiner* — Hanway Chang
(74) *Attorney, Agent, or Firm* — Notaro, Michalos & Zaccaria P.C.

(57) ABSTRACT

Test method checks and compensates ion yield variances in a mass spectrometer and includes feeding an eluate of a chromatographic separation to the spectrometer, continuously admixing a separate target analyte solution at known concentration and constant flow rate to the eluate, injecting the mixture into the spectrometer and generating a detector signal for the mixture. A spectrogram is captured which includes an integration line and a mass-spectrographic peak of the target analyte, the integration line being a lasting background signal underlaid to the mass-spectrometric analysis of the eluate, then evaluating the spectrogram by capturing an integrated mass-spectrographic peak area above the integration line and an area which is found under the integrated peak area of the target analyte by perpendicular drop lines from the peak integration line and forming a mathematical relationship from the determined mass-spectrographic areas.

32 Claims, 2 Drawing Sheets

FUNCTIONAL CHECK AND VARIANCE COMPENSATION IN MASS SPECTROMETRY

RELATED PATENT APPLICATIONS

Figure 1:
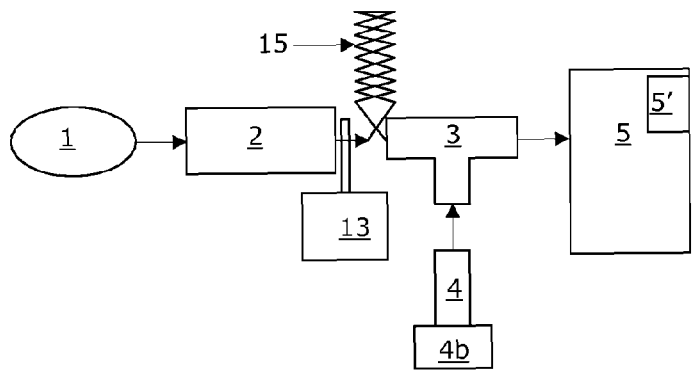

The present patent application claims the priority of the German priority application No. DE 10 2009 030 395.2 of Jun. 25, 2009, the complete content of which shall be included in the present patent application by way of express citation and reference.

FIELD OF TECHNOLOGY

The invention relates to a method for checking the function of a mass spectrometer, to a method for compensating variances in mass spectrometry, and to an apparatus for performing this functional check and compensation method for mass spectrometers.

It concerns an invention in the field of quantitative chemical analysis. An embodiment from the field of biomedical analysis is provided.

Chromatographic and especially chromatographic-mass-spectrometric analytical methods are highly important in the field of life sciences and especially for medical laboratory diagnostics, food and environmental analysis. In this case, biological samples such as plasma, serum, blood or urine is prepared at first (e.g. deproteinized) and then separated by chromatography (e.g. GC=gas chromatography; LC=liquid chromatography; HPLC=high-pressure or high-efficiency liquid chromatography). The sample which was fractioned chromatographically will then continuously be supplied to a mass-spectrometric detector.

In the case of mass spectrometry with atmospheric pressure ionization (e.g. electrospray (ESI) MS/MS), the target analytes are ionized for detection. This ionization however not only detects the respective target analytes, but also a very large number of other substances from the sample matrix. Accordingly, every atmospheric pressure ionization represents a highly complex physicochemical occurrence, in which a plurality of molecular interactions needs to be assumed. This is expressed, among other things, in the phenomenon of "ion suppression" and "ion enhancement". Components of the sample matrix, which in most cases cannot be specified in more detail and which elutes temporally with the respective target analytes into the ion source, can lead both to a reduction and also to an increase in the ion yield of the target analyte. Similarly, deposits on parts of the ion source and the ion optics ("charging") will also lead to the consequence that the ionization efficiency of a system will frequently show a drift or even variation of the detector signal over time (a so-called undulate) within a series of analyses.

RELATED PRIOR ART

Usually, calibrator samples (with known analyte concentrations) are analyzed in a sample series, which calibrator samples are followed by "unknown samples" or "unknowns" to be quantified and by checks. If within such a series there is a drift of the ionization yield with respect to the target analytes within the series of measurement or if the ionization properties differ from the calibrator samples and unknowns, incorrect measurement results of the unknowns will be the consequence.

In order to compensate respective modulation effects of the ion yield, substances are used which are referred to as internal standards. These concern substances which need to be as similar as possible in their molecular structure to the respective target analytes. Ideally suitable are stable isotope-marked molecules of the target analyte (e.g. cortisol molecules in which four hydrogen atoms are exchanged by deuterium) as internal standard for measuring cortisol by means of liquid chromatography-tandem mass spectrometry (LC-MS/MS). In a series of analyses of calibrator or control samples and unknowns, a precisely identical quantity of the respective internal standard is added to all samples (calibrators, controls and unknowns) right at the beginning of the sample processing. As a result, a concentration ratio of target analyte to internal standard is produced for each sample, which ratio no longer changes in the course of the sample processing. In the mass-spectrometric sample run, the signal of target analyte (e.g. collision-induced ion transition in MS/MS technology) and internal standard is recorded in an alternating fashion or simultaneously as a mass spectrogram. Two independent mass spectrograms are therefore recorded in the same sample run. In the case of less specific detection methods such as UV detection, the internal standard must be chosen in such a way that it eluates at a point in time which differs from the target analyte. In this case, two peak areas are determined in a mass spectrogram (analyte and internal standard). For the purpose of quantifying evaluation, the areas of the peaks of internal standard and target analyte are determined (at defined retention times). The ratio of peak area of the target analyte to peak area of the internal standard is known as response of the individual analysis. Calibration and quantification are performed on the basis of this response (i.e. a peak area ratio). As a result of this principle of internal standardization, variances in the ion yield from sample to sample are leveled out at least in part. The precondition for this is however that the ionization behavior of target analyte and internal standard is influenced in a very similar manner by modulating effects ("charging", matrix components, etc).

On the one hand, the use of calibrator samples for quantification leads to an additional input of time for preparation and analysis. On the other hand, such calibrator samples do not provide any direct statements on the quality of the analysis of samples with an unknown concentration of analytes (unknowns).

As an alternative to the addition of a defined quantity of an internal standard to the sample itself as described above (generation of two mass-spectrometric peaks in mass-spectrometric analysis either in the same recording or in simultaneously recorded independent recordings), a method has been described recently in which a reference solution is admixed continuously into the eluate of the chromatographic unit in order to thereby enable a compensation of fluctuations in the ion yield (Stahnke H, Reemtsma T, Alder L "Compensation of matrix effects by post-column infusion of a monitor substance in multiresidue analyses with LC-MS/MS" *Anal. Chem.* 2009, 81: 2185-92). A signal level of the reference substance is recorded periodically (in an alternating manner to the mass transfer track of the target analytes). This reference signal is used with the help of a complex data processing method for measured value compensation with respect to factors which can influence the signal generation.

The method according to Stahnke et al. uses a monitor substance which is not identical to the target analytes. Since the target analyte and the reference substance can differ from one another with respect to their ionization behavior, this approach is principally analytically interference-prone. The search for a suitable reference substance is challenging because a substance needs to be found which under all circumstances is subject to a similar modulation of the signal yield as the target analyte. It has to be assumed for many target analytes that no substances suitable for this purpose can be found. Moreover, a complex evaluation of periodically recorded reference signal and peak area of the target analyte is required, i.e. an evaluation and quantification from the primarily recorded mass spectrogram is not direct possible or is at least interference-prone.

From the book "Introduction To Mass Spectrometry" (Watson & Sparkmann 2007, 4th Edition of John Wiley & Sons Ltd., pages 131-135 and pages 618-622), a calibration is known that always refers to the mass/charge ratio of the molecules (m/z) and their correct capture. Calibration of the mass over a certain range (if MALDI is utilized as ionization method) may be applied as "internal calibration" during capturing the mass spectrogram. In doing so, it is analyzed whether the molecular mass of the detected molecules was captured correctly (m/z expected as compared to m/z measured). The article "How Counting Statistics Controls Detection Limits and Peak Precision" (Gedke, Application Note PerkinElmer Instruments, cited in the Internet on Jul. 20, 2001, pages 1-15) in detail and by employing different mathematical models discusses the influence of background signals on the quality and significance of measured spectrometric courses. In doing so, it is in each case assumed that for estimating detection borders; the detector always functions correctly and in its optimum. In these two documents, quantitative analysis of the amount of molecules for checking their correct capture by the mass spectrometric system with reference to one or several target analytes is not disclosed.

OBJECT AND SUMMARY OF THE PRESENT INVENTION

It is the object of the present invention to provide apparatuses and methods which allow checking the function of a mass spectrometer or the quality of mass-spectrometric analysis and/or allow a compensation of fluctuations in the ion yield.

This object is achieved according to a first aspect in such a way that a test method for checking the function of a mass spectrometer is proposed. The test method in accordance with the invention is characterized in that it comprises the following work steps:

(a) feeding an eluate of a chromatographic separation system and a target analyte solution having a known concentration to a mass spectrometer;
(b) continuous admixing of a separate target analyte solution to the eluate of a chromatographic separation system fed to the mass spectrometer, the separate target analyte solution having a known concentration and being admixed at a constant flow rate;
(c) injecting the mixture produced in step (b) into the mass spectrometer that comprises at least one detector providing a signal and generating a detector signal for the mixture produced in step (b);
(d) capturing a mass spectrogram based on the detector signal generated in step (c), which mass spectrogram comprises an integration line and a mass-spectrographic peak of the target analyte, this integration line being a lasting background signal, which is underlaid to the mass-spectrometric analysis of the eluate;
(e) evaluating the mass spectrogram produced in step (d) by capturing an integrated mass-spectrographic peak area A above the integration line of the target analyte and an area B which is found under the integrated peak area A of the target analyte by perpendicular drop lines from the peak integration line;
(f) forming a mathematical relationship from the determined mass-spectrographic areas A and B evaluated in step (e);
(g) determining a threshold value for the mathematical relationship formed in step (f), which threshold value designates the upper or lower border of the acceptable quality of a mass-spectrometric analysis, and
(h) accepting or rejecting the mass-spectrometric analysis of a sample on the basis of a comparison of the mathematical relationship formed in step (f) with the threshold value determined in step (g).

This object is achieved according to a second aspect in such a way that a method is proposed for the compensation of ion yield variances in mass spectrometry. The compensation method in accordance with the invention is characterized in that it comprises the following work steps:

(a) feeding an eluate of a chromatographic separation system to a mass spectrometer;
(b) continuous admixing of a separate target analyte solution to the eluate of a chromatographic separation system fed to the mass spectrometer, the separate target analyte solution having a known concentration and being admixed at a constant flow rate;
(c) injecting the mixture produced in step (b) into the mass spectrometer that comprises at least one detector providing a signal and generating a detector signal for the mixture produced in step (b);
(d) capturing a mass spectrogram based on the detector signal generated in step (c), which mass spectrogram comprises an integration line and a mass-spectrographic peak of the target analyte, this integration line being a lasting background signal, which is underlaid to the mass-spectrometric analysis of the eluate;
(e) evaluating the mass spectrogram produced in step (d) by capturing an integrated mass-spectrographic peak area A above the integration line of the target analyte and an area B which is found under the integrated peak area A of the target analyte by perpendicular drop lines from the peak integration line;
(f) forming a mathematical relationship from the determined mass-spectrographic areas A and B evaluated in step (e), and
(g) evaluating the mass spectrogram for compensating variances in the ion yield in the detector.

This object is achieved according to a further aspect in such a way that an apparatus is proposed for performing the test method and/or the compensation method. The apparatus in accordance with the invention is characterized in that it comprises:

(a) a pump with a pump control for conveying a solution of a target analyte of known concentration, and
(b) a T-piece configured to be arranged upstream of the mass spectrometer and comprising a first connection for connecting the T-piece with the mass spectrometer, a second connection for connecting the T-piece with the pump, and a third connection for introducing the eluate from a chromatographic separation system, and optionally:
(c) a flow detector.

This object is achieved according to a further aspect in such a way that an apparatus is proposed for performing the test method and/or the compensation method. The apparatus in accordance with the invention is characterized in that it comprises:

(a) a pump with a pump control for conveying a solution of a target analyte of known concentration, and
(b) a feed unit configured to be arranged upstream of the mass spectrometer and comprising a first connection for connecting the feed unit with a vacuum chamber disposed upstream of the mass spectrometer, a first injection conduit with a second connection for introducing the eluate from a chromatographic separation system, and a third connection for connecting the feed unit with the pump, and optionally:
(c) a flow detector.

This object is achieved according to a further aspect in such a way that an apparatus is proposed for performing the test method and/or the compensation method. The apparatus in accordance with the invention is characterized in that it comprises:
(a) a pump with a pump control for conveying a solution of a target analyte of known concentration, and
(b) a mixing unit configured to be arranged upstream of the mass spectrometer and comprising a first connection for connecting the mixing unit with the mass spectrometer, a first injection conduit with a second connection for introducing the eluate from a chromatographic separation system, and a third connection for connecting the mixing unit with the pump, and optionally:
(c) a flow detector.

Additional preferred and/or inventive features are provided from the dependent claims. In doing so, the formation of a quotient A/B, B/A, A-B/A or $A^2/B^2$ or a difference log(A)-log(B) or a respective inverse value is preferable as the mathematical relationship in step (e). The formation of a quotient A/B is especially preferred as the mathematical relationship in step (f) in each case.

BRIEF INTRODUCTION OF THE ATTACHED FIGURES

Figure 2:
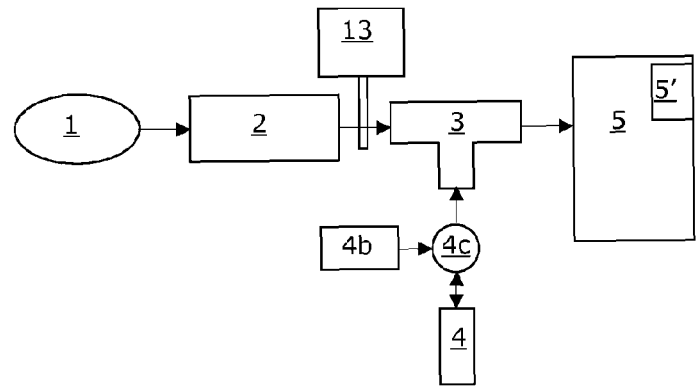
Figure 3:
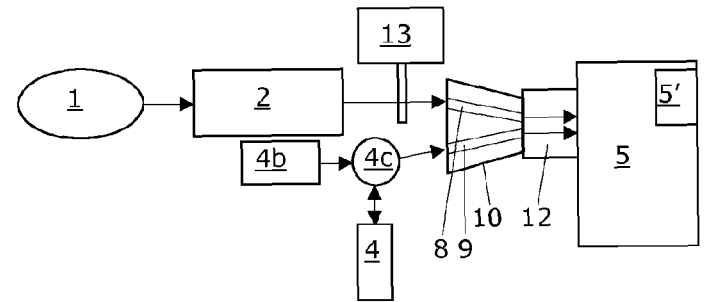
Figure 4:
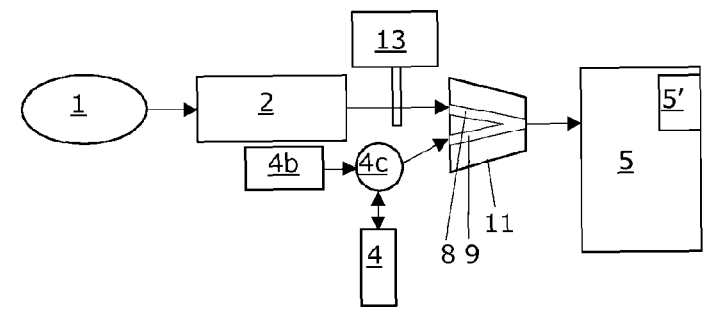
Figure 5:
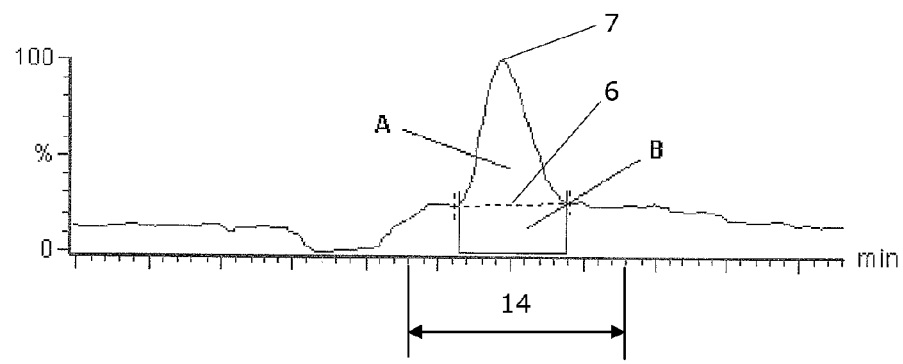
Figure 6:
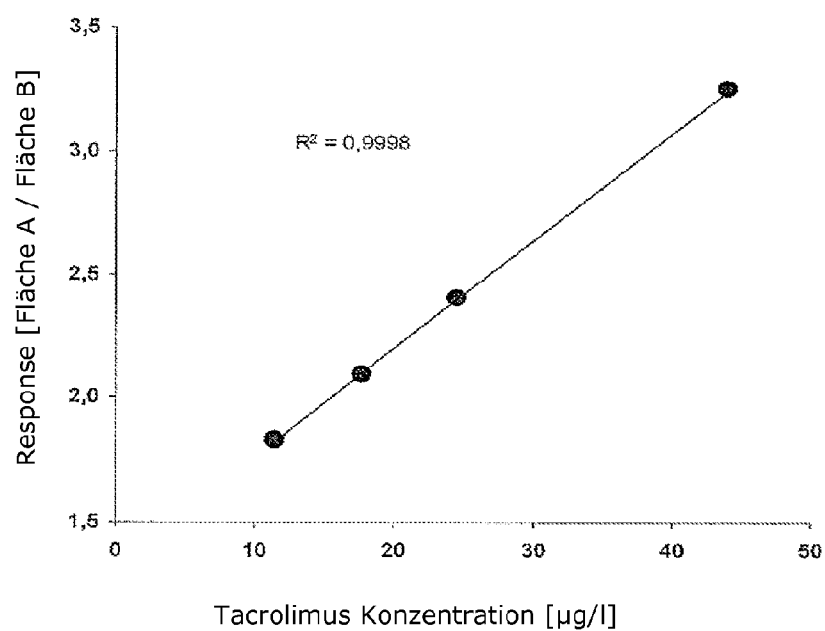

The present invention will be explained in closer detail by reference to schematic drawings and measurement results, with the illustrated embodiments merely being understood as examples and not limiting the scope of the invention, wherein it is shown in:

FIG. 1 a first configuration of a (PCI) system (PCI=permanent post column infusion) for admixing a target analyte to the eluate of a chromatographic separation system;

FIG. 2 a second configuration of a (PCI) system for admixing a target analyte to the eluate of a chromatographic separation system;

FIG. 3 a third configuration of a (PCI) system for admixing a target analyte to the eluate of a chromatographic separation system and comprising a chamber with reduced pressure upstream of the mass spectrometer;

FIG. 4 a fourth configuration of a (PCI) system for admixing a target analyte to the eluate of a chromatographic separation system;

FIG. 5 a mass spectrogram for evaluation according to the described invention, according to which there will be a base line elevation by the continuous addition of a target analyte to the eluate of a chromatographic separation system;

FIG. 6 the calibration function for measuring tacrolimus on the basis of the illustrated technical configuration according to FIG. 1 and the described mass-spectrographic evaluation method.

DETAILED DESCRIPTION OF THE PRESENT INVENTION

A combination of a system configuration and a mass-spectrographic evaluation method was found which allows performing an internal standardization of mass-spectrometric methods solely by using a solution of a target analyte.

This system configuration as is shown in FIGS. 1 to 4 can be used for admixing the target analyte to the eluate of a chromatographic separation system as a reference solution at constant rate. Alternatively, the target analyte (in chromatographic methods with isocratic elution) can be present in a dissolved manner in the mobile phase of the chromatographic system.

It is ensured by the described configurations that the target analyte is supplied to the detector at a continuous flow rate. A continuous "background" signal is produced thereby in the mass spectrometer. The base line is elevated in this process, there is a so-called "base line offset" which underlies the actual mass-spectrometric analysis.

The test method in accordance with the invention can be used to check the function or performance (=performance or response) of a mass spectrometer. The test method in accordance with the invention is based on a base line elevation in the mass spectrogram, which can also be used for compensation of variances in the signal generation of the respective detector concerning the respective target analyte.

Preferably, the check of the function or performance of a mass spectrometer occurs prior to or after the actual sample analyses on the basis of a target analyte solution. The simultaneous or concurrent analysis of a mixture of samples with known analytes and/or unknown analytes and a known target analyte is especially preferred, so that a current quality statement can be made on each analysis. This is achieved in that a separate solution of a target analyte is continuously admixed to the eluate of the chromatographic separation system, so that only this mixture will reach the detector 5' of the mass spectrometer 5.

Different possibilities of this admixing will be explained below:

This admixing of a target analyte to the eluate from a chromatographic separation system 1,2 can occur via a T-piece 3 by means of a pump 4 (see FIG. 1). If said pump 4 has sufficient storage volume (e.g. in the case of a piston pump with a large cylinder volume), no additional reservoir 4b will be required for the target analyte solution. If however a peristaltic pump is used for conveying the target analyte solution to the T-piece 3 (which does not contain any storage volume) then the connection of such a reservoir 4b is inevitable.

If a highly precise syringe pump 4 is used for conveying the target analyte solution then a three-way valve 4c is preferably disposed between the three connections to the T-piece 3, the reservoir 4b and the syringe pump 4 (see FIG. 2). Pumps suitable for use in functional checking or variance compensation are preferably chosen from a group which comprises piezo pumps, syringe pumps, piston pumps (e.g. a known LC pump) and peristaltic pumps. Such pumps are well-known to the person skilled in the art (in the case of piezo pumps from the document EP 0 956 449 B1 for example).

In accordance with a further embodiment of the invention, there is a simultaneous injection of the eluate of the chromatographic separation system and the target analyte solution by means of a double nozzle (known from U.S. Pat. No. 6,465, 776 B1) or feed unit 10 (cf. FIG. 3). Said feed unit 10 comprises two injection conduits 8,9 which are completely separated from one another and of which one injection conduit is charged with the eluate of the chromatographic separation system 1,2 and the other injection conduit is charged with the target analyte solution of the pump 4. This method requires a chamber 12 with reduced pressure which is provided upstream of the mass spectrometer and which is arranged between the feed unit 10 and the mass spectrometer 5. The mixing of the target analyte with the eluate of the chromatic separation system 1,2 (symbolized by a double arrow) only occurs in said upstream vacuum chamber 12. In this case too, only the mixture reaches the detector 5' of the mass spectrometer 5. A quadrupole ion guide, which is not shown here but is known from the U.S. Pat. No. 6,465,776 B1, is preferably arranged between the vacuum chamber 12 and the mass spectrometer 5, with which the individual fluid samples can be brought to a parallel trajectory before they reach the mass spectrometer.

In accordance with a further embodiment of the invention, there is a simultaneous injection of the eluate of the chromatographic separation system 1,2 and the target analyte solution by means of a mixing nozzle (cf. FIG. 4). In contrast to FIG. 3, this mixing unit 11 comprises two injection conduits 8,9 which are separated only partly from one another and of which one injection conduit is supplied with the eluate of the chromatographic separation system 1,2 and the other injection conduit is supplied with the target analyte solution from the pump 4. Both injection conduits join one another within the mixing unit 11, so that a chamber with reduced pressure which is provided upstream of the mass spectrometer can be omitted. In this case too, only the mixture reaches the detector 5' of the mass spectrometer 5.

The following applies generally: the admixing of a target analyte to the eluate from a chromatographic separation system 1,2 via a T-piece 3 or a feed unit 10 or a mixing unit 11 and a separate pump 4 can be used in gradient methods or in isocratic methods.

In accordance with an alternative embodiment of the present invention, the target analyte can be dissolved in the mobile phase of the analytic chromatographic system 1,2, without requiring an additional pump 4. This is possible in the case of isocratic chromatographic analyses.

It can also be provided that the function test is performed only with an analyte solution (without unknowns).

Furthermore, a flow detector 13 with an associated control system can be arranged between the separation column 2 and the T-piece 3 (cf. FIG. 1 and FIG. 2) or between the separation column 2 and the feed unit 10 or the mixing unit 11 (cf. FIGS. 3 and 4). The passing sample or eluate of the chromatographic separation system 1,2 is analyzed continuously with the help of this flow detector 30. The injection of the target analyte into the T-piece 3 or into the feed unit 10 or mixing unit 11 can be commenced upon determining the arrival of interesting samples in the flow detector 13. Upon determining the end of the samples of interest, the injection of the target analyte can be stopped. A time window 14 is defined within the running time of the mass spectrogram by the start and the end of the injection of the target analyte (cf. FIG. 5). This time window is preferably so large that it specifically covers the interesting part of the running time of the mass spectrometer in which the detector signal is captured, which corresponds to an expected analyte.

As a result of the detector-controlled supply of the target analytes, the quantity of often very expensive target analytes which are necessary for performing the test or compensation method in accordance with the invention can be reduced considerably. That is why an apparatus for performing the test method compensation method is preferable which comprises a flow detector 13 with respective control, with the flow detector 13 between the chromatic separation system 1,2 and the T-piece 3 or between the chromatic separation system 1,2 and the feed unit 10 or mixing unit 11 being arranged for the optical analysis of the eluate from the chromatic separation system 1,2. Especially preferred flow detectors 13 are scanning detectors (e.g. UV, VIS and NIR detectors), refractive detectors or fluorescence detectors. The continuous supply of the target analyte at a constant flow rate during the time window 14 which is shorter than the running time of the mass spectrogram can occur in all embodiments shown in FIGS. 1 to 4 of the apparatus in accordance with the invention for performing the test method or compensation method.

This supply of the target analyte can also occur in a time-controlled manner as an alternative to or in combination with the aforementioned detector-controlled supply of the target analyte. This is especially advantageous and can be performed in an especially simple manner if a number of similar substances contained in the samples are to be analyzed in the mass spectrometer.

Preferably, the target analyte reaches the mixing location with the eluate from the chromatographic separation system 1,2 during target analyte supply shortly before the time at which an interesting event from the chromatographic separation system 1,2 also reaches this mixing location. Depending on the chosen embodiment of the apparatus for performing the test method or compensation method, this mixing location can be disposed in the interior of a T-piece 3 (cf. FIGS. 1 and 2), following a supply unit 10 (see vacuum chamber 12 in FIG. 3), or in the interior of a mixing unit 11 (cf. FIG. 4). In order to ensure that sufficient time is available for the supply of the target analyte under these preconditions, the time is preferably extended which is required by the eluate from the chromatographic separation system 1,2 in order to reach the chosen mixing location from the flow detector 13. In the case of a constant flow in the system, an extension of the path between the flow detector 13 and the mixing location in the interior of a T-piece 3, following a feed unit 10, or in the interior of a mixing unit 11 represents a simple solution of this instruction. Such a path extension 15 is achieved for example with a capillary (similar to an HPLC capillary), which is placed for example between the flow detector 13 and the T-piece 3. If a larger path extension 15 is required the capillary can be wound up (cf. FIG. 1). Alternatively and/or additionally, the respective inlet limb of the T-piece 3 can be extended or comprise a labyrinth which extends the path (not shown). The pump 4 for the supply of the target analyte can be put into operation in time in such an apparatus when detecting an interesting event in the flow detector 13. The path extension 15 can also be advantageously used in a time-controlled target analyte supply.

The evaluation of the obtained mass spectrograms will be explained below in closer detail:

In the evaluation of these mass spectrograms, the peak area A of the target analyte (which is generated by the actual mass-spectrometric process) is captured by established methods of base point recognition and area measurement. In addition, the "base" (i.e. the area B of the quadrangle) beneath the respective peak will be captured (cf. FIG. 5). The "response" of the individual analysis is preferably calculated as the quotient of the peak area A to peak area B of the quadrangle beneath the peak 7. This area B is formed by the integration line 6 of the peak 7, the base line of the mass spectrogram and the drop lines which are dropped from the ends of the peak integration line 6 to the baseline (cf. FIG. 5; areas A and B).

If the ionization efficiency concerning the target analyte decreases or increases in the period of the elution of the analyte peak 7, a reduction or increase in the recorded peak area A is obtained. Similarly, a reduction or increase in the area B of the base beneath the peak is also obtained. As a result, the quotient of the two areas A/B will become independent of the momentary ion yield. The method is therefore suitable to cancel out variances in the ion yield, as also applies to distinct internal standard substances which are added to a sample before the analysis. If the concentrations of the analytes in the sample and in the elution solution are known, the quotient of the two areas A/B or any other mathematical relationship such as the quotient of the squares of these areas $A^2/B^2$ or the value of any other previously mentioned mathematical relationship of the areas A and B allows making a statement on the quality of the analysis.

The described method further offers relevant and surprising advantages over the state of the art, because the possibility is provided to develop chromatographic and especially mass-spectrometric analytical methods without requiring separate substances for internal standardization for this purpose: the monitor substance (either added to the mobile phase or added post-column to the flow) is identical with the respective target analytes in the described method.

A reduction in the workload during sample preparation is achieved as compared with conventional methods of internal standardization with the addition of the internal standard within the scope of sample preparation. There is a further advantage in the case of mass-spectrometric methods (especially also compared to the method according to Stahnke et al) that only one single mass track needs to be recorded per analyte for the quantification. If the system configuration is used in which the target analyte is dissolved in the mobile phase (as described here), there is a relevant advantage over the method according to Stahnke et al that no additional equipment items are required.

The search for a reference substance which is very similar to the target analyte in its signaling properties represented a relevant challenge up until now in the development of respective methods: if no suitable reference substances are found, the development of specific mass-spectrometric methods will often fail entirely. Therefore, the invention relevantly improves the applicability of quantitative chromatographic/mass-spectrometric analytical methods in chemical analysis.

The functional performance of the method will be demonstrated on the basis of an embodiment by the measurement of the immunosuppressive tracrolimus from human whole blood samples. Four calibrator samples were used for this purpose in the therapeutic concentration range after protein precipitation. These precipitates were analyzed by means of LC-MS/MS (description of the method: Vogeser, Michael et al. 2008 "Instrument-specific matrix effects of calibration materials in the LC-MS/MS analysis of tacrolimus" *Clin. Chem.* 54: 1406-8). A solution of tacrolimus (100 μg/l in methanol/water, 1/1) was infused at a flow rate of 5 μl/min via a T-piece into the fluid flow between analytic column and mass-spectrometry system (according to FIG. 1).

FIG. 5 shows a mass spectrogram recorded over its entire running period. A mass transfer specific for tacrolimus is detected thereby (mother ion 821.5 m/q; product ion 768.5 m/q). The area A is the peak area. The area B is the base area beneath the peak which is generated by the continuous tacrolimus infusion. The areas A and B can be calculated both from the analog as well as digital signals or the data of the mass spectrometer detector.

FIG. 6 shows the calibrating function which was prepared on the basis of this mass-spectrographic evaluation. The known analyte concentrations of the calibrator samples were entered on the X axis. The Y axis shows the respective response as a peak area ratio of surface A/surface B. A linear relationship between the peak area response and calibrator concentrations is obtained. A quality control sample analyzed in this series on the basis of the illustrated principle was found within the target range specified by the manufacturer within a concentration of 5.2 μg/l.

Especially preferred embodiments of the method for compensating ion yield variances in mass spectrometry comprise the following features:

A differentiated chromatographic analytical method for compensating variances in the signal-generating unit in quantifying chromatographic analyses is characterized in that the signal-generating unit (the detector) is supplied with a pure solution of the target analyte of the measurement during a series of analyses at a continuous and constant flow rate.

Furthermore, such a chromatographic analytical method is preferably characterized in that a background signal is generated in this manner in the chromatogram (=base line elevation, offset).

Moreover, such chromatographic analytical methods are preferably characterized in that the continuous supply of the target analyte is achieved either in such a way that the target analyte is dissolved in the mobile phase of the chromatographic system (in methods with isocratic elution) or that a solution of the target analyte is admixed as a reference substance continuously and at a constant flow rate into the flow distally of the analytic separation column by a T-piece and a second pump unit.

Furthermore, such chromatographic analytical methods are preferably characterized in that the thus achieved base line elevation in the chromatogram is utilized for compensating variances of signal generation of the respective detector concerning the respective target analyte.

Furthermore, such chromatographic analytical methods are preferably characterized in that the quadrangle beneath the integration line of the peak of the target analyte is evaluated.

Finally and especially preferred, such chromatographic analytical methods are characterized in that for quantifying the target analyte the area which is found by perpendicular drop lines from the peak integration line beneath the integrated chromatographic peak of the target analyte is placed in an evaluation method in relationship with the integrated peak area above the integration line of the target analyte for the purpose of quantifying target analytes.

Useful combinations of the illustrated and described embodiments belong to the scope of the present invention.

List of reference numerals:

| | | |
|---|---|---|
| 1 | HPLC pump | Chromatographic separation system |
| 2 | Separation column | |
| 3 | T-piece | |
| 4 | Pump | |
| 4b | Reservoir | |
| 4c | Three-way valve | |
| 5 | Mass spectrometer | |
| 5' | Signal-generating detector of 5 | |
| 6 | Integration line of 7 | |
| 7 | Mass-spectrographic peak | |
| 8 | First separate injection conduit | |
| 9 | Second separate injection conduit | |
| 10 | Feed unit | |
| 11 | Mixing unit | |
| 12 | Vacuum chamber | |
| 13 | Flow detector | |
| 14 | Time window | |
| 15 | Path extension | |
| A | Peak area of the target analyte (above the integration line 6) | |
| B | Area beneath the integration line of 7 by perpendicular drop lines (as base line elevation) | |

The invention claimed is:

1. A test method for checking the function of a mass spectrometer (5), characterized in that it comprises the following work steps:
   (a) feeding an eluate of a chromatographic separation system (1, 2) to a mass spectrometer (5);

(b) continuous admixing of a separate target analyte solution to the eluate of a chromatographic separation system (1, 2) fed to the mass spectrometer,
the separate target analyte solution having a known concentration and being admixed at a constant flow rate;
(c) injecting the mixture produced in step (b) into the mass spectrometer (5) that comprises at least one detector (5') providing a signal and generating a detector signal for the mixture produced in step (b);
(d) capturing a mass spectrogram based on the detector signal generated in step (c), which mass spectrogram comprises an integration line (6) and a mass-spectrographic peak (7) of the target analyte, this integration line being a lasting background signal, which is underlaid to the mass-spectrometric analysis of the eluate;
(e) evaluating the mass spectrogram produced in step (d) by capturing an integrated mass-spectrographic peak area (A) above the integration line (6) of the target analyte and an area (B) which is found under the integrated peak area (A) of the target analyte by perpendicular drop lines from the peak integration line (6);
(f) forming a mathematical relationship from the determined mass-spectrographic areas A and B evaluated in step (e);
(g) determining a threshold value for the mathematical relationship formed in step (f), which threshold value designates the border of the acceptable quality of a mass-spectrometric analysis, and
(h) accepting or rejecting the mass-spectrometric analysis of a sample on the basis of a comparison of the mathematical relationship formed in step (f) with threshold value determined in step (g).

2. The test method according to claim 1, characterized in that the mathematical relationship is chosen from a group which comprises the quotients (A/B), (B/A), (A-B/A) or $(A^2/B^2)$, and the difference [log(A)-log(B)] and its respective inverse values.

3. The test method according to claim 1, characterized in that the mathematical relationship is defined by the quotient (A/B).

4. The test method according to claim 1, characterized in that the continuous supply of the target analyte occurs at a constant flow rate during a time window (14) which is shorter than the running time of the mass spectrogram.

5. The test method according to claim 1, characterized in that the continuous supply of the target analyte occurs by a pump (4) which is in operative connection with a T-piece (3) arranged upstream of the mass spectrometer (5).

6. The test method according to claim 1, characterized in that a target analyte is dissolved in the mobile phase of the chromatographic separation system (1, 2).

7. The test method according to claim 1, characterized in that a separate solution of a target analyte and the eluate of the chromatographic separation system (1, 2) are supplied continuously and at a constant flow rate during the mass-spectrometric analysis via separate injection conduits (8, 9) to a feed unit (10), a vacuum chamber (12) and then mass-spectrometric analysis.

8. The test method according to claim 7, characterized in that the continuous supply of the target analyte occurs at a constant flow rate during a time window (14) which is shorter than the running time of the mass spectrogram.

9. An apparatus for performing the test method according to claim 7, characterized in that the apparatus comprises:
(a) a pump (4) with a pump control for conveying a solution of a target analyte of known concentration, and
(b) a feed unit (10) configured to be arranged upstream of the mass spectrometer (5) and comprising a first connection for connecting the feed unit (10) with a vacuum chamber (12) disposed upstream of the mass spectrometer (5), a first injection conduit (8) with a second connection for introducing the eluate from a chromatographic separation system (1, 2), and a third connection for connecting the feed unit (10) with the pump (4), and optionally:
(c) a flow detector (13).

10. The test method according to claim 1, characterized in that a separate solution of a target analyte and the eluate of the chromatographic separation system (1, 2) are supplied continuously and at a constant flow rate during the mass-spectrometric analysis via converging injection conduits (8, 9) to a mixing unit (11), are mixed in said mixing unit with one another, and are then supplied to mass-spectrometric analysis.

11. An apparatus for performing the test method according to claim 10, characterized in that the apparatus comprises:
(a) a pump (4) with a pump control for conveying a solution of a target anayte of known concentration, and
(b) a mixing unit (11) configured to be arranged upstream of the mass spectrometer (5) and comprising a first connection for connecting the mixing unit (11) with the mass spectrometer (5), a first injection conduit (8) with a second connection for introducing the eluate from a chromatographic separation system (1, 2), and a third connection for connecting the mixing unit (11) with the pump (4), and optionally:
(c) a flow detector (13).

12. An apparatus for performing the test method according to claim 1, characterized in that the apparatus comprises:
(a) a pump (4) with a pump control for conveying a solution of a target analyte of known concentration, and
(b) a T-piece (3) configured to be arranged upstream of the mass spectrometer (5) and comprising a first connection for connecting the T-piece (3) with the mass spectrometer (5), a second connection for connecting the T-piece with the pump (4), and a third connection for introducing the eluate from a chromatographic separation system (1, 2), and optionally:
(c) a flow detector (13).

13. The apparatus according to claim 12, characterized in that it further comprises a reservoir (4b) for the solution of the target analyte.

14. The apparatus according to claim 13, characterized in that it further comprises a three-way valve (4c), which is arranged between the pump (4) and the reservoir (4b), and the T-piece (3) or a feed unit (10) or a mixing unit (11).

15. The apparatus according to claim 12, characterized in that the pump is chosen from a group which comprises piezo pumps, syringe pumps, piston pumps and peristaltic pumps.

16. The apparatus according to claim 12, characterized in that it comprises a flow detector (13) with associated control, with the flow detector (13) being arranged between the chromatographic separation system (1, 2) and the T-piece (3), or between the chromatographic separation system (1, 2) and a feed unit (10), or between the chromatographic separation system (1, 2) and a mixing unit (11), and is configured for the optical analysis of the eluate from the chromatographic separation system (1, 2).

17. A method for compensating ion yield variances in mass spectrometry, characterized in that it comprises the following work steps:
(a) feeding an eluate of a chromatographic separation system (1, 2) to a mass spectrometer (5);

(b) continuous admixing of a separate target analyte solution to the eluate of a chromatographic separation system (1, 2) fed to the mass spectrometer (5), the separate target analyte solution having a known concentration and being admixed at a constant flow rate;

(c) injecting the mixture produced in step (b) into the mass spectrometer (5) that comprises at least one detector (5') providing a signal and generating a detector signal for the mixture produced in step (b);

(d) capturing a mass spectrogram based on the detector signal generated in step (c), which mass spectrogram comprises an integration line (6) and a mass-spectrographic peak (7) of the target analyte, this integration line being a lasting background signal, which is underlaid to the mass-spectrometric analysis of the eluate;

(e) evaluating the mass spectrogram produced in step (d) by capturing an integrated mass-spectrographic peak area (A) above the integration line (6) of the target analyte and an area (B) which is found under the integrated peak area A of the target analyte by perpendicular drop lines from the peak integration line (6);

(f) forming a mathematical relationship from the determined mass-spectrographic areas (A) and (B) evaluated in step (e), and (g) evaluating the mass spectrogram for compensating variances in the ion yield in the detector (5').

18. The compensation method according to claim 17, characterized in that the mathematical relationship is chosen from a group which comprises the quotients (A/B), (B/A), (A-B/A) or ($A^2/B^2$), and the difference [log(A)-log(B)] and its respective inverse values.

19. The compensation method according to claim 17, characterized in that the mathematical relationship is defined by the quotient (A/B).

20. The compensation method according to claim 17, characterized in that the continuous supply of the target analyte occurs at a constant flow rate during a time window (14) which is shorter than the running time of the mass spectrogram.

21. The compensation method according to claim 17, characterized in that the continuous supply of the target analyte occurs by a pump (4) which is in operative connection with a T-piece (3) arranged upstream of the mass spectrometer (5).

22. The compensation method according to claim 17, characterized in that a target analyte is dissolved in the mobile phase of the chromatographic separation system (1, 2).

23. The compensation method according to claim 17, characterized in that a separate solution of a target analyte and the eluate of the chromatographic separation system (1, 2) are supplied continuously and at a constant flow rate during the mass-spectrometric analysis via separate injection conduits (8, 9) to a feed unit (10), a vacuum chamber (12) and then mass-spectrometric analysis.

24. An apparatus for performing the compensation method according to claim 23, characterized in that the apparatus comprises:

(a) a pump (4) with a pump control for conveying a solution of a target analyte of known concentration, and (b) a feed unit (10) configured to be arranged upstream of the mass spectrometer (5) and comprising a first connection for connecting the feed unit (10) with a vacuum chamber (12) disposed upstream of the mass spectrometer (5), a first injection conduit (8) with a second connection for introducing the eluate from a chromatographic separation system (1, 2), and a third connection for connecting the feed unit (10) with the pump (4), and optionally:

(c) a flow detector (13).

25. The compensation method according to claim 17, characterized in that a separate solution of a target analyte and the eluate of the chromatographic separation system (1, 2) are supplied continuously and at a constant flow rate during the mass-spectrometric analysis via converging injection conduits (8, 9) to a mixing unit (11), are mixed in said mixing unit with one another, and are then supplied to mass-spectrometric analysis.

26. The compensation method according to claim 25, characterized in that the continuous supply of the target analyte occurs at a constant rate during a time window (14) which is shorter than the running time of the mass spectrogram.

27. An apparatus for performing the compensation method according to claim 25, characterized in that the apparatus comprises:

(a) a pump (4) with a pump control for conveying a solution of a target analyte of known concentration, and (b) a mixing unit (11) configured to be arranged upstream of the mass spectrometer (5) and comprising a first connection for connecting the mixing unit (11) with the mass spectrometer (5), a first injection conduit (8) with a second connection for introducing the eluate from a chromatographic separation system (1, 2), and a third connection for connecting the mixing unit (11) with the pump (4), and optionally:

(c) a flow detector (13).

28. An apparatus for performing the compensation method according to claim 17, characterized in that the apparatus comprises:

(a) a pump (4) with a pump control for conveying a solution of a target analyte of known concentration, and (b) a T-piece (3) configured to be arranged upstream of the mass spectrometer (5) and comprising a first connection for connecting the T-piece (3) with the mass spectrometer (5), a second connection for connecting the T-piece with the pump (4) and a third connection for introducing the eluate from a chromatographic separation system (12), and optionally:

(c) a flow detector (13).

29. The apparatus according to claim 28, characterized in that it further comprises a reservoir (4b) for the solution of the target analyte.

30. The apparatus according to claim 29, characterized in that it further comprises a three-way valve (4c), which is arranged between the pump (4) and the reservoir (4b), and the T-piece (3) or a feed unit (10) or a mixing unit (11).

31. The apparatus according to claim 28, characterized in that the pump is chosen from a group which comprises piezo pumps, syringe pumps, piston pumps and peristaltic pumps.

32. The apparatus according to claim 28, characterized in that it comprises a flow detector (13) with associated control, with the flow detector (13) being arranged between the chromatographic separation system (1, 2) and the T-piece (3), or between the chromatographic separation system (1, 2) and a feed unit (10), or between the chromatographic separation system (1, 2) and a mixing unit (11), and is arranged for the optical analysis of the eluate from the chromatographic separation system (1, 2).

\* \* \* \* \*